(12) United States Patent
Smith (10) Patent No.: US 11,324,529 B2
(45) Date of Patent: May 10, 2022

(54) HANDHELD SURGICAL DEVICE HAVING A ROTATING PORTION

(71) Applicant: Michael D. Smith, Tonka Bay, MN (US)

(72) Inventor: Michael D. Smith, Tonka Bay, MN (US)

( * ) Notice: Subject to any disclaimer, the term of this patent is extended or adjusted under 35 U.S.C. 154(b) by 133 days.

(21) Appl. No.: 16/345,100

(22) PCT Filed: Oct. 25, 2017

(86) PCT No.: PCT/US2017/058266
§ 371 (c)(1),
(2) Date: Apr. 25, 2019

(87) PCT Pub. No.: WO2018/081253
PCT Pub. Date: May 3, 2018

(65) Prior Publication Data
US 2019/0282258 A1 Sep. 19, 2019

Related U.S. Application Data

(60) Provisional application No. 62/412,976, filed on Oct. 26, 2016.

(51) Int. Cl.
*A61B 17/32* (2006.01)
*A61B 17/16* (2006.01)
(Continued)

(52) U.S. Cl.
CPC .......... *A61B 17/32* (2013.01); *A61B 17/1626* (2013.01); *A61B 17/1628* (2013.01); *A61B 17/1631* (2013.01); *A61B 17/32002* (2013.01); *A61B 17/320708* (2013.01); *A61B 17/1604* (2013.01); *A61B 17/1659* (2013.01); *A61B 2017/00353* (2013.01);
(Continued)

(58) Field of Classification Search
CPC .... A61B 17/320708; A61B 17/320783; A61B 17/32002; A61B 17/1659; A61B 17/1615; A61B 17/3494
See application file for complete search history.

(56) References Cited

U.S. PATENT DOCUMENTS 3,734,207 A * 5/1973 Fishbein ............ A61B 17/1622
173/217
4,986,807 A * 1/1991 Farr ............... A61B 17/320783
604/22
(Continued)

OTHER PUBLICATIONS

Extended European Search Report, European patent application No. 17863705.4, dated Jul. 12, 2019 (8 pages).
(Continued)

*Primary Examiner* — David W Bates
(74) *Attorney, Agent, or Firm* — Greenberg Traurig, LLP (57) ABSTRACT

A handheld surgical device with a working portion driven by a motor, wherein the working portion is contained in a concave-shaped portion when it is not activated, and the working portion becomes exposed from the concave-shaped portion when it is activated. The activation of the working portion can be controlled by a switch located at a handle portion of the handheld surgical device. The handheld surgical device includes a concave-shaped portion with a cutting edge, which is not driven by the motor.

13 Claims, 5 Drawing Sheets

(51) Int. Cl.
*A61B 17/3207* (2006.01)
*A61B 90/00* (2016.01)
*A61B 1/00* (2006.01)
*A61B 17/00* (2006.01)

(52) U.S. Cl.
CPC ............. *A61B 2017/320008* (2013.01); *A61B 2017/320766* (2013.01); *A61B 2017/320791* (2013.01); *A61B 2090/08021* (2016.02)

(56) References Cited

U.S. PATENT DOCUMENTS

| | | | | |
|---|---|---|---|---|
| 5,217,479 | A * | 6/1993 | Shuler | A61B 17/32002 600/564 |
| 8,469,981 | B2 * | 6/2013 | Robertson | A61B 17/320068 606/169 |
| 8,480,675 | B2 * | 7/2013 | Betts | A61B 17/1671 606/84 |
| 8,945,021 | B2 * | 2/2015 | Chin | A61B 90/37 600/564 |
| 2003/0229343 | A1 | 12/2003 | Albrecht et al. | |
| 2004/0191897 | A1 | 9/2004 | Muschler | |
| 2004/0243157 | A1 * | 12/2004 | Connor | A61M 1/0084 606/159 |
| 2006/0074425 | A1 * | 4/2006 | Sutterlin | A61B 17/025 606/79 |
| 2009/0112119 | A1 | 4/2009 | Kim | |
| 2009/0228030 | A1 | 9/2009 | Shadeck | |
| 2010/0030216 | A1 | 2/2010 | Arcenio | |
| 2012/0101513 | A1 * | 4/2012 | Shadeck | A61B 17/1659 606/170 |
| 2013/0197551 | A1 | 8/2013 | Yoon et al. | |
| 2014/0277040 | A1 | 9/2014 | Hayes et al. | |
| 2015/0250495 | A1 | 9/2015 | Robertson et al. | |
| 2015/0282833 | A1 | 10/2015 | Yoon et al. | |
| 2017/0196573 | A1 | 7/2017 | Smith | |

OTHER PUBLICATIONS

International Search Report and Written Opinion, PCT/US2017/058266, dated Jan. 3, 2018 (6 pages).

* cited by examiner

HANDHELD SURGICAL DEVICE HAVING A ROTATING PORTION

FIELD

This disclosure relates generally to a handheld surgical device configured for performing one or more surgical procedure(s).

BACKGROUND

Surgical tools are used in the healthcare field to, for example, affect (e.g., cut, remove, cauterize, etc.) an anatomical part during a surgical procedure. Generally, each surgical tool is configured to perform a specific function. Accordingly, it can be necessary for a professional to use multiple surgical tools during a surgical procedure when different functions are needed to complete the surgical procedure.

SUMMARY

When a healthcare professional uses multiple surgical tools, manual actions of switching between the two surgical tools can be very time consuming and can lead to an increase in associated costs.

The disclosure herein provides improved handheld surgical devices and methods related to handheld surgical devices. Some of the embodiments of the handheld surgical devices described herein are configured with a working portion that is contained (when not in operation), and then exposed (when in operation). The term "contained" is used herein can mean that an element is located or positioned to be protected or covered by another structure, at least partially or entirely. Accordingly, a working portion that is contained can mean that, at least a part of or all of, the working portion is protected or covered by another structure (e.g., a concave-shaped portion, a hooded cover, or a partially enclosed scoop).

For example, the working portion can be contained in a concave-shaped portion when the working portion is not in operation. When the working portion is activated, at least a part of the working portion becomes exposed from the concave-shaped portion so that at certain times, the working portion is not covered by the concave-shaped portion.

For example, a working portion having a cutting blade is configured to rotate about its major axis when activated (e.g., powered, turned on, etc.). When not activated, the working portion is contained in a concave-shaped portion such that the cutting blade of the working portion is covered by the concave-shaped portion. When activated, the working portion rotates, and the rotation of the working portion causes the cutting blade of the working portion to become exposed from the concave-shaped portion so that the rotating cutting blade can cut materials without being hindered by the concave-shaped portion.

Further, when the working portion is contained, the part (e.g., concave-shaped portion) that covers the working portion can include another working portion that is configured for performing a different procedure. Thus, some of the embodiments of the handheld surgical devices can be used to perform two or more specific functions. Advantageously, the embodiments of the handheld surgical devices described herein can reduce or eliminate the need for switching between surgical devices during performance of a surgical procedure. Thus, there can be savings in time, related costs, or both.

The handheld surgical device has a distal portion and a proximal portion. The terms "proximal" and "distal" are used herein to indicate portions of the handheld surgical device with respect to an operator's hand. In other words, when in use, the proximal portion is closer to the operator's hand than the distal portion of the handheld surgical device. The proximal portion includes a handle configured for being held by an operator's hand.

In an embodiment, a switch is disposed at the proximal portion (e.g., handle), and the switch is configured to operate a motor to rotate a shaft in the distal portion such that the working portion connected to the shaft rotates. In other embodiments, the switch may be disposed at a different position, such as for example, at the distal portion.

In another embodiment, the handheld surgical device is activated by a remote switch, such as for example, a foot pedal switch (wired or wireless) configured to activate the motor of the handheld surgical device when the foot pedal switch is activated by a foot, or a similar device. Accordingly, in some embodiments, a switch is not disposed at the proximal portion of the handheld surgical device.

In another embodiment, a switch is disposed at the proximal portion (e.g., handle) and a remote switch (e.g., foot pedal switch, etc.) are both be included in the handheld surgical device. The concave-shaped portion is configured to protect nearby anatomical part(s) when the working portion is activated. When the switch turns off the motor, the motor is configured to ensure that the working portion is contained in the concave-shaped portion (e.g., the cutting blade(s) of the working portion is contained in the concave-shaped portion when the motor is not activated to rotate the shaft).

In some embodiments, the shaft is balanced (e.g., with a counterweight).

BRIEF DESCRIPTION OF THE DRAWINGS

References are made to the accompanying drawings that form a part of this disclosure, and which illustrates the embodiments in which the devices and methods described herein can be practiced.

DETAILED DESCRIPTION

Generally, a working portion of a handheld surgical device is configured for performing a specific function during a medical procedure that is performed by a healthcare professional. During the medical procedure, it can be necessary for the healthcare professional to switch between different handheld surgical devices at the same or near an anatomical location. For example, a device for cutting and removing soft tissue may be used, and then, when that device nears a bone, a different device may be needed to cut away the bone. Switching between different handheld surgical devices repeatedly within the wound to complete an operation can increase the operation time and associated costs. Further, switching between different surgical devices may require the healthcare professional to take her eyes off of the anatomical region (e.g., wound) and also may require additional mental concentration in order to acquire the correct tool for the needed function in the anatomical region. Accordingly, alternating between several tools can be tedious and may increase the fatigue of the healthcare professional, risk of contamination, infection, and/or damage to the patient. The contamination, infection, and/or unintended damage can cause or exacerbate problems for a patient and a treatment plan. Thus, there is a clear advantage for a handheld surgical device which can reduce and/or eliminate the tedious alternation between different tools.

The handheld surgical devices described herein can provide multiple tools and/or functions in a single device. Thus, the handheld surgical devices described herein can reduce and/or eliminate the tedious alternation between different tools.

An embodiment of a handheld surgical device described herein includes a concave-shaped portion with a cutting edge disposed on a distal portion, wherein the concave-shaped portion can contain a working portion with a cutting blade. When the working portion is activated (e.g., powered on) via a switch connected to a control unit, motor, and a power supply, the motor rotates a shaft, which in turn rotates the working portion about the major axis of the shaft. The rotation of the working portion exposes the cutting blade of the working portion from the concave-shaped portion (i.e., the cutting blade becomes not contained as the working portion is activated). The working portion and the shaft are rotationally balanced (e.g., with a counterweight disposed on the shaft).

Figure 1:
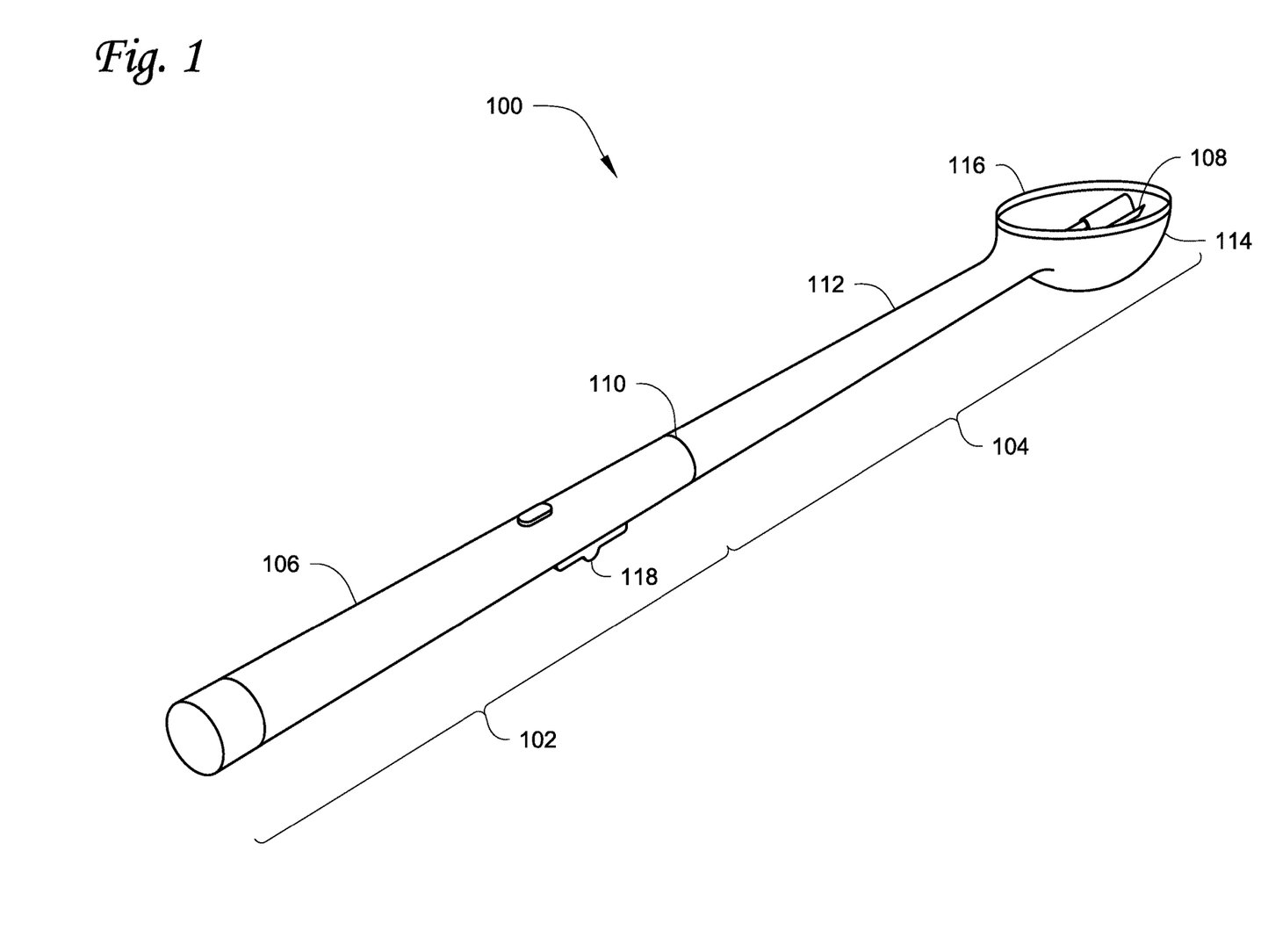
FIG. 1 depicts a schematic illustration of an embodiment of the handheld surgical device.

FIG. 1 depicts a schematic illustration of a handheld surgical device 100 according to an embodiment. The handheld surgical device 100 includes a proximal portion 102 and a distal portion 104. The proximal portion 102 includes a handle 106 configured for an operator's hand to hold, preferably comfortably, while the handheld surgical device 100 is being used. The distal portion 104 includes a working portion 108. At least a part of the working portion 108 is configured for being inserted into a wound or an anatomical area to perform a function (e.g., cut bone, cut tissue, etc.) during a surgical procedure.

In some embodiments, the distal portion 104 can be attached to or detached from the proximal portion 102 at an attachment region 110. For example, the distal portion 104 can be detached from the proximal portion 102 at the attachment region 110 after use in a surgical procedure, and then a new (i.e., unused) distal portion 104 can be attached to the proximal portion 102 at the attachment region 110 before being used in another surgical procedure. Alternatively, the distal portion 104 can be removed and cleaned/sanitized before being reattached to the proximal portion 102 for future use. That is, the distal portions 104 can be disposed of after use, or be sanitized after use for reuse.

The distal portion 104 includes a neck portion 112, which extends from the attachment region 110 to the working portion 108. The working portion 108 of the handheld surgical device 100 can be contained with a concave-shaped portion 114 disposed at or near the end of the distal portion 104. The concave-shaped portion 114 can be, for example, bowl-shaped and have a cutting edge 116. In some embodiments, the concave-shaped portion 114 can be a hooded cover, or be a partially enclosed scoop. For example, the cutting edge 116 and the concave-shaped portion 114 can be used for cutting and/or scooping soft tissue, without requiring a powered motor. The working portion 108 is connected to a motor and a power supply so that the working portion 108 can be activated for cutting harder tissue than soft tissue (e.g., bone, etc.).

Advantageously, a healthcare professional can use the handheld surgical device 100 for at least two different functions (e.g., for affecting different anatomical regions). Thus, the handheld surgical device 100 can eliminate the need for manually switching between two different surgical tools (e.g., for cutting soft tissue and for cutting bone) during a surgical procedure.

As described further herein, the working portion 108 can be exposed above a cutting edge 116 of the concave-shaped portion 114 by, for example, being activated to rotate within the concave-shaped portion 114. The proximal portion 102 of the handheld surgical device 100 includes a switch 118 disposed at or near the handle 106. Although not shown, some embodiments may include the switch may be disposed at a different position, such as for example, at the distal portion. The switch 118 is connected to a control unit in the handle 106 connected to a motor, which in turn is connected to a shaft inside the neck portion 112. The shaft is connected to the working portion 108, so that when the switch 118 is activated, the control unit powers the motor for rotating the shaft and the working portion 108. The handheld surgical device 100 can be of various shapes and sizes.

Figure 2:
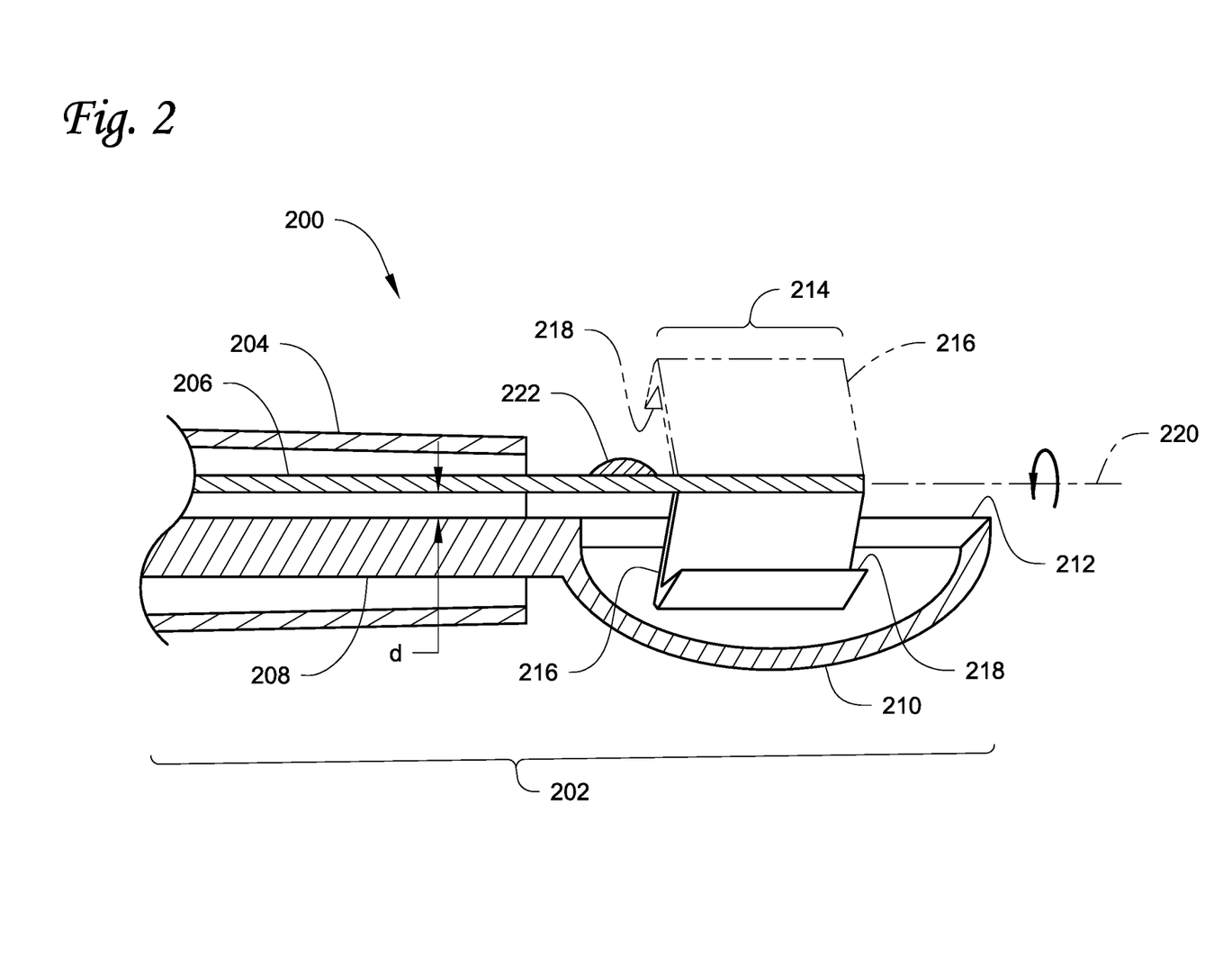
FIG. 2 depicts a schematic view of a portion of a distal portion of the handheld surgical device according to an embodiment.

FIG. 2 depicts a schematic view of a portion of a handheld surgical device 200. The distal portion 202 of the handheld surgical device 200 includes a housing 204 that encases a shaft 206 and an extension 208. The shaft 206 and the extension 208 are separated by a distance (d) within the housing 204. In an embodiment, the distance is greater than 0 cm. In some embodiments, the extension 208 and the housing 204 can be combined together, and in such case, the distance between the shaft 206 and a major central axis of the distal portion 202 can be expressed by the distance (d).

The extension 208 includes or is connected to a concave-shaped portion 210 with a cutting edge 212. The concave-shaped portion 210 includes a concave structure with a bowl-shape. The bowl-shape of the concave-shaped portion 210 can have an enclosed lower surface, rounded sides, and an opening on an upper surface.

The shaft 206 is connected to a working portion 214. The working portion 214 includes one or more extension(s) 216 that extends along a radial direction away from the shaft 206, and each of the extension(s) 216 has a cutting blade 218 extending along a circumferential direction (or perpendicularly with respect to the extension 216 connected to the cutting blade 218) with respect to the shaft 206. Accordingly, when the shaft 206 rotates, the cutting blade 218 rotates for cutting (e.g., bone, flesh, etc.).

In some embodiments, shaft 206 can have two or more extensions 216, each of the extensions 216 having a respective cutting blade 218.

The shaft 206 is configured to rotate about its axis of rotation 220 when in operation (e.g., powered on, activates, etc.), as indicated by the arrow and axis in FIG. 2. When in operation the shaft 206 rotates the cutting blade 218 about the axis of rotation 220 of the shaft 206. As the cutting blade 218 is rotated about the axis 220 of the shaft 206, the cutting blade 218 becomes exposed as they rise above the cutting edge 212 of the concave-shaped portion 210. In FIG. 2, this state of exposed cutting blade 218 is shown in dashed lines. In other words, during a round of rotation, the cutting blade 218 of the working portion 214 becomes higher than a cutting edge 212 of the concave-shaped portion 210.

The powered rotation of the cutting blade 218 can cut tissue, bone, or a combination of tissue and bone, which otherwise would be difficult or impossible to cut with the cutting edge 212. For example, the cutting blade 218 can act to tear, gouge, or chisel tissue, bone, or a combination of tissue and bone. The cutting blade 218 can be composed of one or a combination of surgical stainless steel, or other materials.

When the working portion 214 is not in operation (e.g., not in use), the motor connected to the shaft 206 stops to ensure that all of the one or more extension(s) 216 are directed away or directed substantially away from the opening of the concave-shaped portion 210, so that the cutting blade 218 is contained in the concave-shaped portion 210 (i.e., the cutting blade 218 is towards the bottom surface of the concave-shaped portion 210). For example, the cutting blade 218 is positioned so as to be located close to the lower surface of the bowl-shape and away from the opening on the upper surface. In other words, the cutting blade 218 of the working portion 214 is substantially surrounded by the concave-shaped portion 210. In FIG. 2, this state of contained cutting blade 218 is shown in solid lines. This allows for the cutting edge 212 of the concave-shaped portion 210 to be used (e.g., for cutting or scooping of soft tissue, or for a combination of cutting and scooping soft tissue) without being hindered by the cutting blade 218 of the working portion 216. The shaft 206 can include a counterweight portion 222 disposed on the shaft 206 to rotationally balance the working portion 214.

Figure 3A:
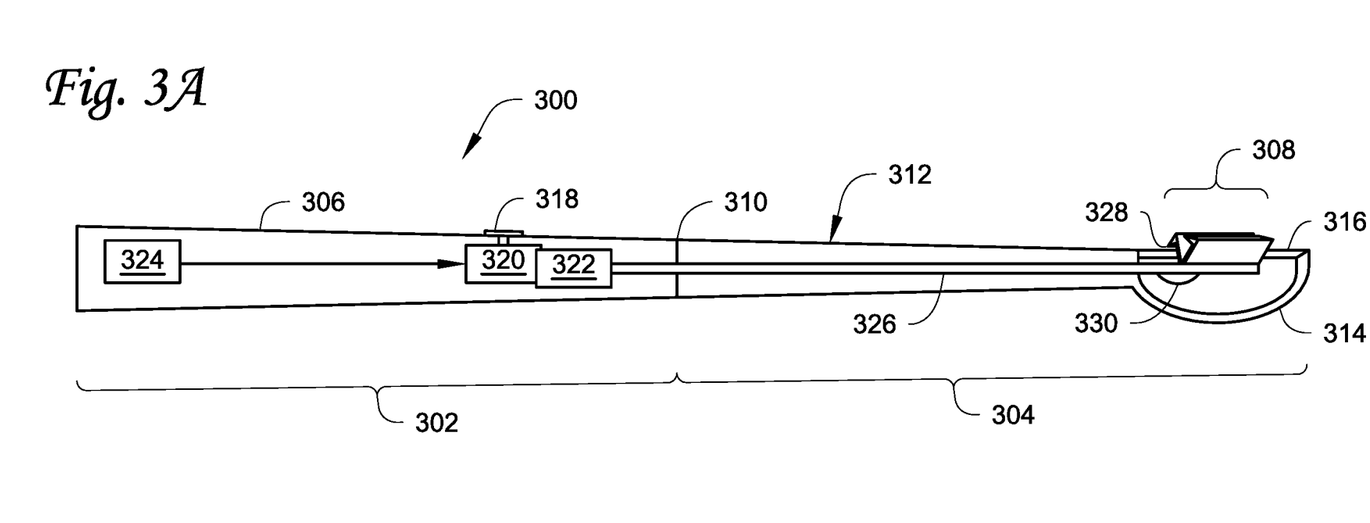
FIGS. 3A and 3B depict schematic side views of an embodiment of the handheld surgical device.
Figure 3B:
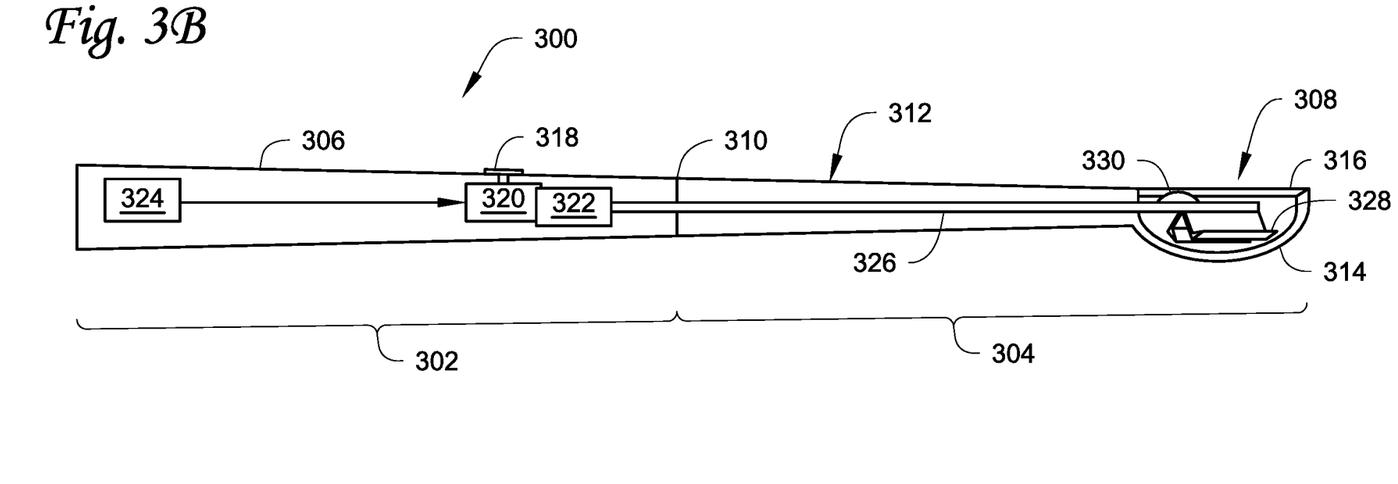

FIGS. 3A and 3B depict schematic side views of a handheld surgical device 300, according to an embodiment. The handheld surgical device 300 includes a proximal portion 302, a distal portion 304, a handle 306, a working portion 308, an attachment region 310, a neck portion 312, a concave-shaped portion 314, a cutting edge 316, and a switch 318, wherein these elements are similar to the like features shown and described with respect to FIG. 1.

The proximal portion 302 includes a control mechanism 320 that is connected to the switch 318 and to a motor 322. The motor 322 and the control mechanism 320 are connected to a power supply 324 (e.g., a battery) for supplying power to the motor 322. When the switch 318 is activated, the control mechanism 320 allows powering of the motor 322, which rotates a shaft 326 connected to the motor 322 and the working portion 308.

Rotating the working portion 308 rotates a cutting blade 328 of the working portion 308. FIG. 3A shows the cutting blade 328 exposed out of the concave-shaped portion 314 (e.g., the motor is activated). FIG. 3B shows a state of the motor having been powered down (i.e., the shaft 326 is not rotating), and in this state, one or more of the control mechanism 320 and the motor 322 ensures that the cutting blade 328 is contained in the concave-shaped portion 314, so that the cutting blade 328 is not in the way of the cutting edge 316.

The shaft 326 can include a counterweight portion 330 disposed on the shaft 326 to rotationally balance the working portion 308.

Figure 4A:
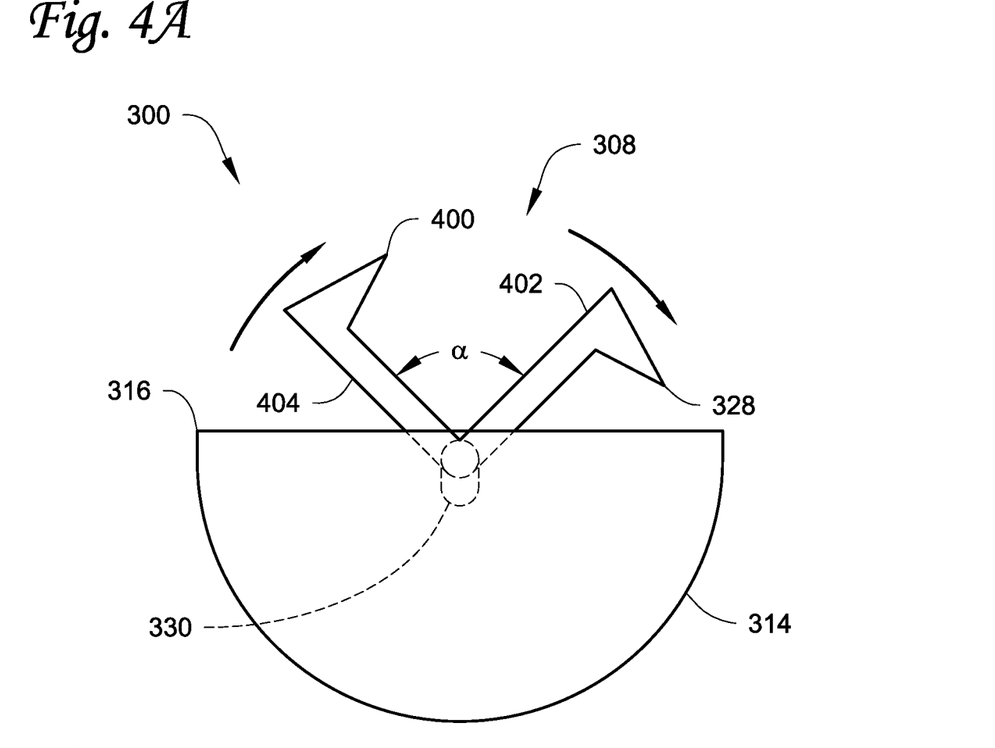
FIGS. 4A and 4B depict schematic end views of the distal portion of the embodiment of the handheld surgical device shown in FIGS. 3A and 3B.

FIG. 4A shows the distal portion end view of the handheld surgical device 300 shown in FIG. 3A, showing the cutting blade 328 exposed out of the concave-shaped portion 314 as the cutting blade 328 rotates. In this view, an angle of the minor arc between the cutting blade 328 and a second cutting blade 400 of the working portion 208 is less than 180 degrees. Another way of describing this is that the angle (α) of the minor arc between respective extensions 402, 404 of the cutting blades 328, 400 is less than 180 degrees, in this view.

Figure 4B:
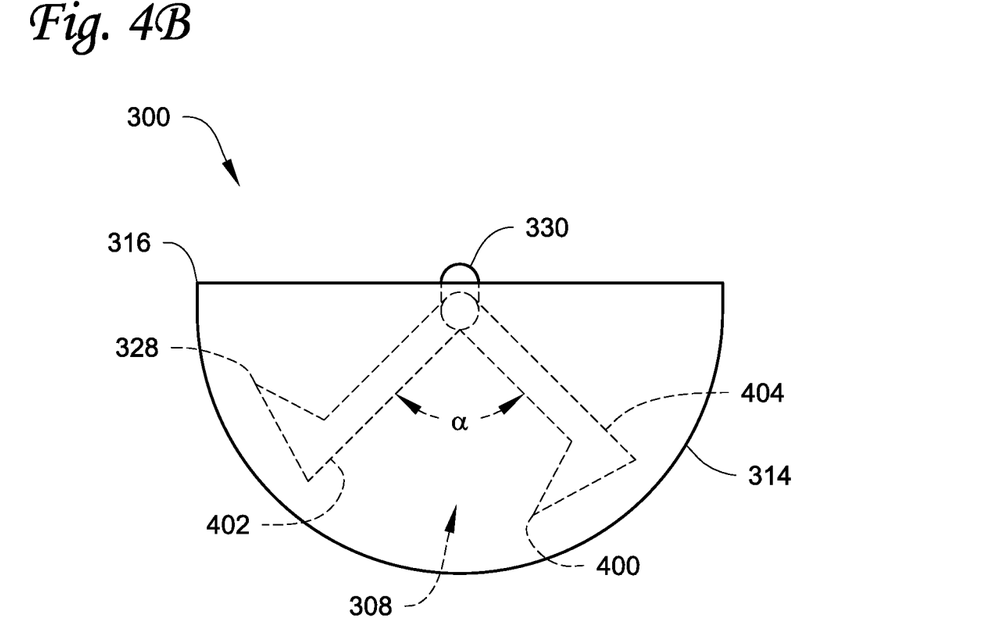

FIG. 4B shows the distal portion end view of the handheld surgical device 300 shown in FIG. 3B, showing the cutting blade 328 contained in the concave-shaped portion 314 when the motor has been powered down (i.e., the shaft 326 is not rotating).

Figure 5:
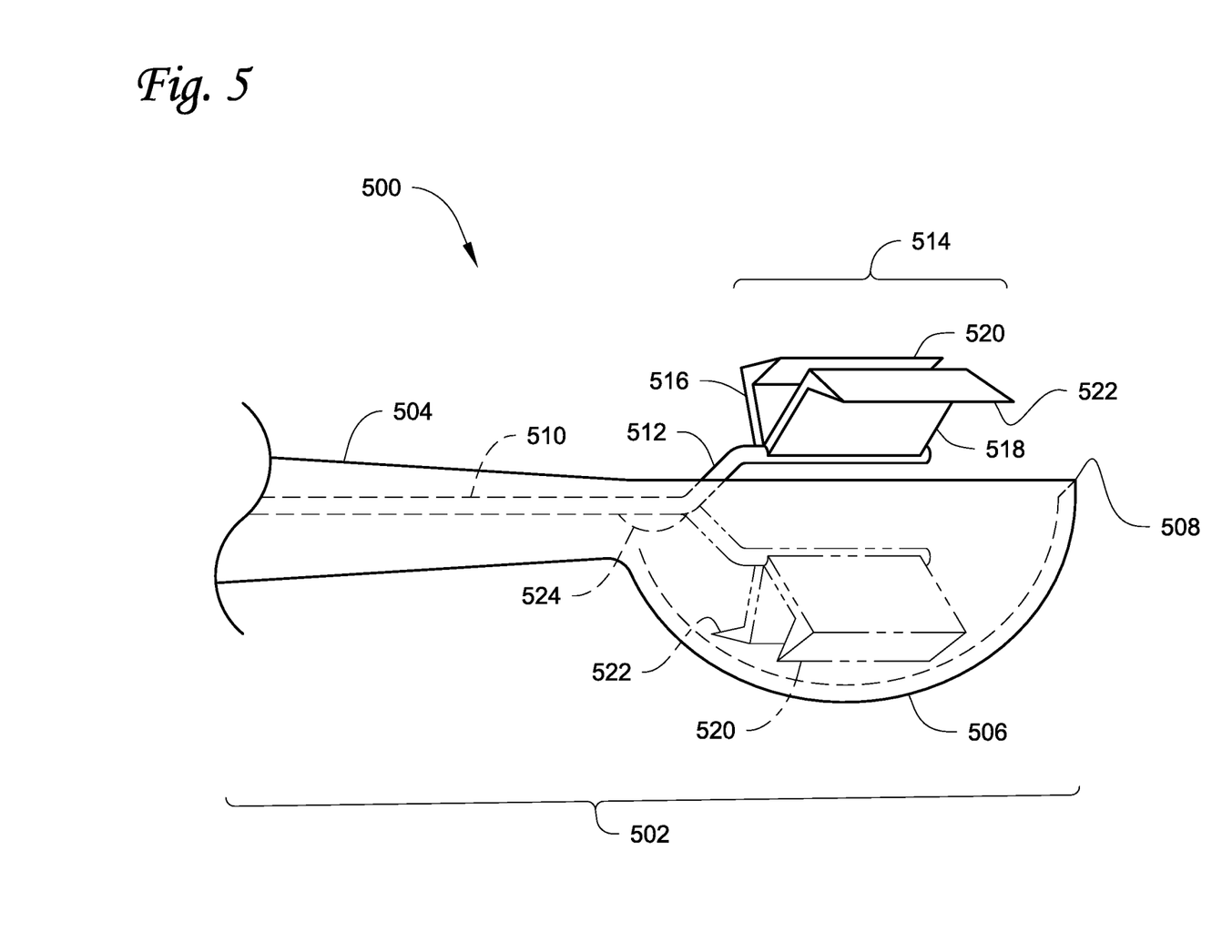
FIG. 5 depicts a schematic view of another embodiment of a portion of the distal portion of the handheld surgical device.

FIG. 5 shows a schematic view of another embodiment of the handheld surgical device 500. The distal portion 502 includes a neck 504 connected to a concave-shaped portion 506. The concave-shaped portion 506 has a cutting edge 508 near an opening.

The neck 504 encases a shaft 510 has a curved or bent-twice portion 512 between the shaft 510 and the working portion 514. The working portion 514 includes at least two extensions 516, 518, each of the extensions having a respective cutting blade 520, 522.

The shaft 510 is configured to rotate when in operation (e.g., powered on, activates, etc.). When in operation, the shaft 510 rotates the curved or bent-twice portion 512 so that the cutting blades 520, 522 become exposed out of the concave-shaped portion 506. In other words, during a round of rotation of the shaft 510, the cutting blades 520, 522 become higher than a cutting edge 508 of the concave-shaped portion 506. In FIG. 5, this state of exposed cutting blades 520, 522 is shown in solid lines.

When the working portion 514 is not in operation (i.e., powered off so that the shaft 510 is not rotating), the cutting blades 520, 522 are located close to the lower surface of the concave-shaped portion 506 to be contained in the concave-shaped portion 506. This allows for the cutting edge 508 of the concave-shaped portion 506 to be used without being hindered by the cutting blades 520, 522.

The shaft 510 includes a counterweight portion 524 disposed on the shaft 510 to rotationally balance the working portion 514.

The terminology used in this Specification is intended to describe particular embodiments and is not intended to be limiting. The terms "a," "an," and "the" include the plural forms as well, unless clearly indicated otherwise.

Aspects:

Any of the following aspects can be combined with any one or more of the other aspects.

Aspect 1. A handheld surgical device, comprising:
  a distal portion including a concave-shaped portion with a cutting edge, and a working portion; and
  a proximal portion including a control mechanism, a power supply, and a motor connected together, the control mechanism controls power supplied to or not supplied from the power supply to the motor, and the motor being connected to a shaft extending towards the working portion and being connected thereto, wherein when the motor is not activated by power from the power supply, the working portion is contained in the concave-shaped portion.

Aspect 2. The handheld surgical device of aspect 1, wherein when the motor is activated by power from the power supply, the motor rotates the shaft and the working portion so that a portion of the working portion becomes exposed out from the concave-shaped portion as the working portion rotates.

Aspect 3. The handheld surgical device of any one or more of aspects 1-2, wherein the working portion includes an extension connected to a cutting blade, wherein the extension distances the cutting blade along a radial direction from the shaft.

Aspect 4. The handheld surgical device of any one or more of aspects 1-3, wherein the working portion includes:
   a first extension connected to a first cutting blade, wherein the first extension distances the first cutting blade along a radial direction from the shaft; and
   a second extension connected to a second cutting blade, wherein the second extension distances the second cutting blade along the radial direction from the shaft.

Aspect 5. The handheld surgical device of any one or more of aspects 1-4, wherein an angle ($\alpha$) of a minor arc defined by the first extension and the second extension is less than 180 degrees.

With regard to the preceding description, it is to be understood that changes may be made in detail, especially in matters of the construction materials employed and the shape, size, and arrangement of parts without departing from the scope of the present disclosure. The embodiments described are exemplary only. Other and further embodiments may be devised without departing from the basic scope thereof, with the true scope and spirit of the disclosure being indicated by the claims.

What is claimed is:

1. A handheld surgical device, comprising:
   a distal portion including:
      a concave-shaped portion having a cutting edge, and
      a working portion connected to a shaft, wherein the working portion includes:
         a first extension connected to a first cutting blade, wherein the first extension distances the first cutting blade along a radial direction from the shaft; and
         a second extension connected to a second cutting blade,
            wherein the second extension distances the second cutting blade along the radial direction from the shaft, and
         wherein an angle (a) of a minor arc defined by the first extension and the second extension is less than 180 degrees;
   a proximal portion including:
      a motor,
      wherein when the motor is not activated by power, the working portion is contained in the concave-shaped portion.

2. The handheld surgical device of claim 1, wherein when the motor is activated by power, the motor rotates the shaft and the working portion so that a portion of the working portion becomes exposed out from the concave-shaped portion as the working portion rotates.

3. The handheld surgical device of claim 1, wherein the proximal portion further includes a control mechanism and a power supply.

4. The handheld surgical device of claim 3, wherein the control mechanism, the power supply, and the motor are connected together.

5. The handheld surgical device of claim 3, wherein the power supply is a battery.

6. The handheld surgical device of claim 3, wherein the control mechanism controls power supplied to or not supplied from the power supply to the motor.

7. A handheld surgical device, comprising:
   a distal portion including:
      a concave-shaped portion having a cutting edge, and
      a working portion connected to a shaft, wherein the working portion includes:
         a first extension connected to a first cutting blade, wherein the first extension distances the first cutting blade along a radial direction from the shaft; and
         a second extension connected to a second cutting blade,
            wherein the second extension distances the second cutting blade along the radial direction from the shaft, and
         wherein an angle (a) of a minor arc defined by the first extension and the second extension is less than 180 degrees; and
   a proximal portion including:
      a motor,
      wherein when the motor is not activated, the working portion is contained in the concave-shaped portion.

8. The handheld surgical device of claim 7, wherein the proximal portion further includes a control mechanism.

9. The handheld surgical device of claim 8, wherein the control mechanism and the motor are connected together.

10. The handheld surgical device of claim 8, wherein the control mechanism controls the motor.

11. The handheld surgical device of claim 7, wherein the proximal portion further includes a power supply.

12. The handheld surgical device of claim 11, wherein the power supply is a battery.

13. The handheld surgical device of claim 7, wherein the shaft includes a counterweight portion disposed on the shaft and configured to rotationally balance the working portion.

* * * * *